(12) United States Patent
Lin

(10) Patent No.: US 11,684,645 B2
(45) Date of Patent: Jun. 27, 2023

(54) ACTINIDIA CHINENSIS PLANCH FERMENT AND USE THEREOF

(71) Applicant: TCI CO., LTD, Taipei (TW)

(72) Inventor: Yung-Hsiang Lin, Taipei (TW)

(73) Assignee: TCI CO., LTD., Taipei (TW)

( * ) Notice: Subject to any disclaimer, the term of this patent is extended or adjusted under 35 U.S.C. 154(b) by 210 days.

(21) Appl. No.: 16/695,254

(22) Filed: Nov. 26, 2019

(65) Prior Publication Data

US 2021/0154251 A1    May 27, 2021

(51) Int. Cl.
*A61K 36/185* (2006.01)
*A61P 1/14* (2006.01)

(52) U.S. Cl.
CPC .............. *A61K 36/185* (2013.01); *A61P 1/14* (2018.01)

(58) Field of Classification Search
None
See application file for complete search history.

(56) References Cited

U.S. PATENT DOCUMENTS

2017/0326190 A1* 11/2017 Ansell ................... A23L 19/01

FOREIGN PATENT DOCUMENTS

| CN | 105962343 A | * | 9/2016 | ......... A23V 2002/00 |
| CN | 105962343 A | | 9/2016 | |

OTHER PUBLICATIONS

Ma, T. et al. Jan. 16, 2019. Comparison of the nutritional properties and biological activities of kiwifruit (Actinidia) and their different forms of products: towards making kiwifruit more nutritious and functional. Food & Function 10: 1317-1329; specif. pp. 1317, 1318,1322, 1323, 1324, 1325.*

Lee, Y. et al. 2011. Antioxidant and glycation inhibitory activities of gold kiwifruit, Actinidia chinensis. Journal of the Korean Society for Applied Biological Chemistry 54(3): 460-467; specif. pp. 460, 463, 464.*

Kuda, T. et al. 2016. Anti-glycation properties of the aqueous extract solutions of dried algae products and effect of lactic acid fermentation on the properties. Food Chemistry 192: 1109-1115; specif. p. 1109.*

Lee, S. et al. 2017. Semi-continuous fermentation of onion vinegar and its functional properties. Molecules 22(1313): 1-16; specif. pp. 1, 2, 5, 6, 7.*

EngMT—Zhao, Z.-F. et al. Kiwi fruit enzyme and preparation method thereof. Chinese Patent Application Publication No. CN105962343; Publication Date: Sep. 28, 2016. pp. 1-16; specif. pp. 2, 3, 4, 5, 6, 11, 14.*

Examination report dated Sep. 22, 2022, listed in correspondent China patent application No. 201910651206.3 (publication No. CN 110934290 A).

* cited by examiner

*Primary Examiner* — Renee Claytor
*Assistant Examiner* — Sharon M. Papciak
(74) *Attorney, Agent, or Firm* — Chieh-Mei Wang

(57) ABSTRACT

The present invention provides an *Actinidia chinensis* Planch ferment and the use thereof in a composition for increasing the antioxidant activity, increasing the anti-glycation activity, increasing the activity of proteolytic enzymes, improving the gastrointestinal dyspepsia, and increasing the gastrointestinal flora diversity. The *Actinidia chinensis* Planch ferment is prepared by fermenting *Actinidia chinensis* Planch extract with yeast, lactic acid bacteria and acetic acid bacteria in a three-staged fermentation.

2 Claims, 3 Drawing Sheets

ACTINIDIA CHINENSIS PLANCH FERMENT AND USE THEREOF

BACKGROUND OF THE INVENTION

1. Field of the Invention

The present invention relates to an *Actinidia chinensis* Planch ferment and a use thereof, and more particularly to the *Actinidia chinensis* Planch ferment for preparing a pharmaceutical composition of increasing antioxidant activity, increasing anti-glycation activity, increasing activity of proteolytic enzymes, improving gastrointestinal dyspepsia, increasing diversity of gastrointestinal flora.

2. The Prior Art

The main function of gastrointestinal tract is to break down food and absorb nutrients. However, stress increasing in modern life and eating habits changing cause many people to suffer from functional dyspepsia. The so-called functional dyspepsia refers to symptoms of upper abdominal pain, upper abdominal bloating, loss of appetite, nausea, vomiting, and upper abdominal discomfort, etc.; however, after examination, there are no organic lesions (such as peptic ulcer, stomach cancer, etc.), and the symptoms would still continue or recurs. There are still no drugs or methods for treating functional dyspepsia. Patients can be only be recommended to improve their diet habits (such as avoiding overeating and eating less digestible foods), as well as maintaining proper exercise and maintaining normal routines to improve the functional dyspepsia.

In addition, the gastrointestinal tract is also an important immune organ of individuals. It is an important shield against the entry of pathogens into the body. Therefore, the health of the gastrointestinal tract is closely related to the health of individuals. The health of the gastrointestinal tract is not only affected by the flora of the gastrointestinal tract, but also the antioxidant capacity of the gastrointestinal cells themselves. Studies have shown that when the environmental pressure factors (such as pathogens) in the gastrointestinal tract are excessive, they cause oxidative stress, which can cause damage to the integrity of the gastrointestinal tract, inflammation, and even flora changes. The gastrointestinal cells with good antioxidant activity are closely linked to each other (tight junction), which can reduce the pathogen and toxins moving between intestinal cells in the first line of defense, and the strong cells are less affected by the inflammatory reaction; therefore, once the antioxidant capacity of the gastrointestinal tract cells is deteriorated, the immunity is reduced, and the intestinal digestion and metabolic functions are also affected, which may even cause chronic inflammatory reactions or alter the intestinal flora and cause many other diseases. Therefore, improving the antioxidant capacity of the gastrointestinal tract is also a key point in maintaining the health of the gastrointestinal tract and maintaining its normal function.

Advanced glycation end products (AGEs) are a group of highly oxidized compounds and are therefore considered to be a glycol-toxin. Studies have shown that advanced glycation end products bind to receptors on the cell surface and alter their structure and function. It also promotes the increase of oxidative stress and inflammatory reaction of cells, and is more inseparable from the formation of diabetes, arteriosclerosis and chronic kidney diseases. In addition to the advanced glycation end products produced from normal metabolism, many processed foods also contain advanced glycation end products. Studies have also pointed out that avoiding the intake of advanced glycation end products from food can slow down the progression of chronic diseases and aging.

In summary, in response to changes in the gastrointestinal or overall health problems faced by modern lives due to changes in living styles and eating habits, and based on the improvement of living standards and the improvement of the concept of health care, it is necessary to develop a pharmaceutical composition which can effectively improve the symptoms of gastrointestinal dyspepsia, increase antioxidant activity, and increase anti-glycation activity.

SUMMARY OF THE INVENTION

To solve the foregoing problem, one objective of the present invention is to provide an *Actinidia chinensis* Planch ferment obtained by a method comprising: extracting an *Actinidia chinensis* Planch with water to obtain an *Actinidia chinensis* Planch extract; fermenting the *Actinidia chinensis* Planch extract sequentially with *Saccharomyces cerevisiae*, *Lactobacillus plantarum*, and *Acetobacter aceti*; and separating the *Actinidia chinensis* Planch ferment.

The other objective of the present invention is to provide a method of improving gastrointestinal discomfort symptoms, comprising administering to a subject in need thereof an effective amount of the *Actinidia chinensis* Planch ferment.

The other objective of the present invention is to provide a method of increasing an antioxidant activity and an anti-glycation activity, comprising administering to a subject in need thereof an effective amount of the *Actinidia chinensis* Planch ferment.

The other objective of the present invention is to provide a method of increasing an activity of proteolytic enzyme, improving gastrointestinal dyspepsia, and increasing a diversity of gastrointestinal flora, comprising administering to a subject in need thereof an effective amount of a pharmaceutical composition containing the *Actinidia chinensis* Planch ferment.

The other objective of the present invention is to provide a method of preparation of a *Actinidia chinensis* Planch ferment, comprising: extracting *Actinidia chinensis* Planch with water to obtain an *Actinidia chinensis* Planch extract; fermenting the *Actinidia chinensis* Planch extract sequentially with *Saccharomyces cerevisiae*, *a-Lactobacillus plantarum*, and an *Acetobacter aceti*; and separating the *Actinidia chinensis* Planch ferment.

In one embodiment of the present invention, the *Saccharomyces cerevisiae* is BCRC20271; the *Lactobacillus plantarum* is DSM33108; and the *Acetobacter aceti* is BCRC11688; the *Saccharomyces cerevisiae* is added with 0.01-0.5% (v/v); the *Lactobacillus plantarum* is added with 0.01-0.25% (v/v); and the *Acetobacter aceti* is added with 3-10% (v/v); and a ratio of the fermentation time of the *Saccharomyces cerevisiae* stage, the *Lactobacillus plantarum* stage, and the *Acetobacter aceti* stage is 1-2.5:1-3:3-10.

In one embodiment of the present invention, the improving gastrointestinal discomfort symptoms is to increase an activity of a proteolytic enzyme.

In one embodiment of the present invention, the increasing an antioxidant activity is to increase an activity of superoxide dismutase or increase a total amount of polyphenol.

Meanwhile, the pharmaceutical composition of the present invention for increasing antioxidant activity, increasing anti-glycation activity, increasing the activity of proteolytic enzyme, improving gastrointestinal dyspepsia, and increasing the diversity of gastrointestinal flora can further comprise an effective amount of the *Actinidia chinensis* Planch ferment and a pharmaceutically acceptable carrier, and the is in a form of a powder, a granule, a solution, a gel or a paste.

The *Actinidia chinensis* Planch ferment of the invention can be effectively used for preparing a pharmaceutical composition for increasing antioxidant activity, increasing anti-glycation activity, increasing the activity of proteolytic enzyme, improving gastrointestinal dyspepsia, and increasing the diversity of gastrointestinal flora. The *Actinidia chinensis* Planch ferment can not only effectively improve the function of the gastrointestinal tract to maintain the normal operation of the gastrointestinal immune function but also slow down the progression of chronic diseases and aging. The *Actinidia chinensis* Planch ferment can also increase the function of gastrointestinal digestion to achieve the function of strengthening the stomach and maintaining the normal function of the intestines.

The embodiments of the present invention are further described with the following drawings. The following embodiments are given to illustrate the present invention and are not intended to limit the scope of the present invention, and those having ordinary skill in the art can make some modifications and refinements without departing from the spirit and scope of the present invention. Therefore, the scope of the present invention is defined by the scope of the appended claims.

DETAILED DESCRIPTION OF THE PREFERRED EMBODIMENT

Figure 1:
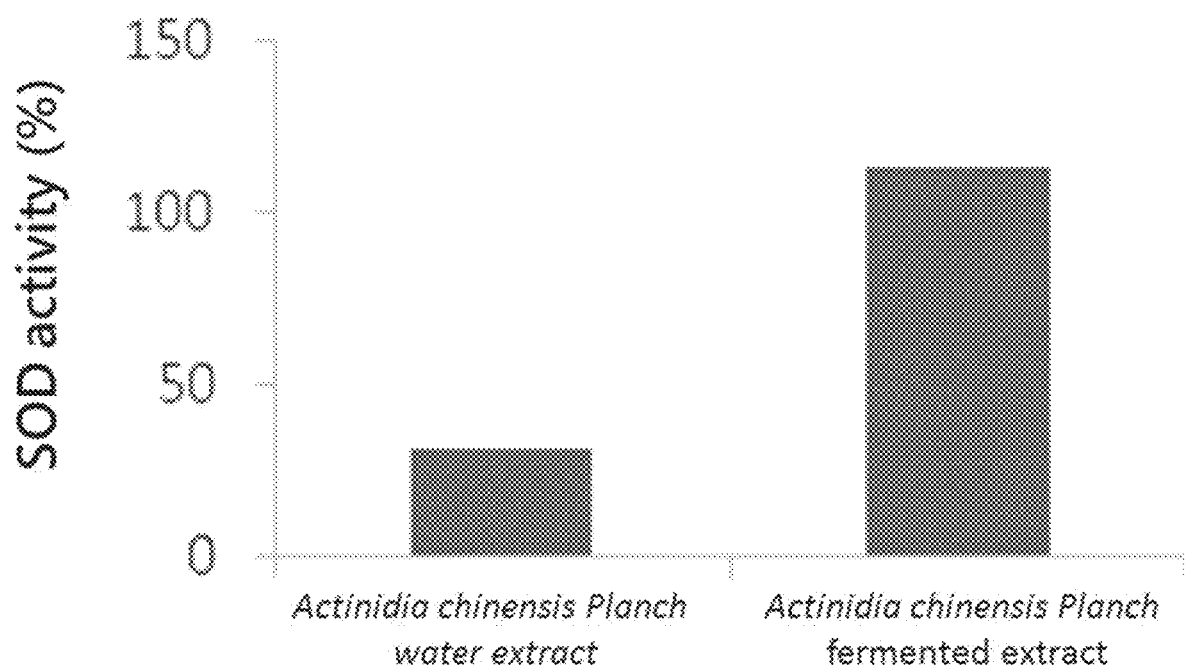
FIG. 1 shows a bar graph that the *Actinidia chinensis* Planch ferment increases the superoxide dismutase activity.

The data provided in the present invention represent approximated, experimental values that may vary within a range of ±20%, preferably ±10%, and most preferably ±5%.

Example 1

Preparation of the *Actinidia chinensis* Planch Ferment

*Actinidia chinensis* Planch is an Actinidiaceae genus *Actinidia* species plant. *Actinidia chinensis* Planch also known as Chinese kiwi, kiwi, carambola, sheep peach, vine pear or rope pear. *Actinidia chinensis* Planch is native to China and grows in the mountains of 400-2,000 meters above sea level. The stalk of it is elongated and with many branches; the leaves appear round or broadly elliptical; the flowers are solitary or several clusters, white at the beginning, and then turned yellow; the fruit is a berry with an oblong, oval or round shape with dense brown furry; the seeds are dark brown. It is known that the stem of *Actinidia chinensis* Planch tree can clear away heat, effect diuresis, promote blood circulation, reduce swelling and anti-cancer.

In one embodiment of the present invention, the fruits of *Actinidia chinensis* Planch were thoroughly washed, and the washed fruits were mixed with water with a solid-liquid ratio of 1:5-15, and then be extracted at 50-100° C. for 0.5-2.5 hours to obtain a *Actinidia chinensis* Planch water extract. The *Actinidia chinensis* Planch water extract was cooled to room temperature for subsequent three-staged fermentation. First, 0.01-0.5% of yeast (*Saccharomyces cerevisiae*, purchased from the Bioresource Collection and Research Center, Taiwan, number BCRC20271) was implanted into the *Actinidia chinensis* Planch water extract for 1-2.5 days fermentation. Then, 0.01-0.25% *Lactobacillus* (*Lactobacillus plantarum* TCI028, patent deposited in Deutsche Sammlung von Mikroorganismen und Zellkulturen (DSMZ; Inhoffenstr. 7B, D-38124 Braunschweig, Germany) on May 2, 2019, and the number is DSM33108) was directly implanted into the previous ferment for another 1-3 days fermentation. Next, 3-10% *Acetobacter* (*Acetobacter aceti*, purchased from the Bioresource Collection and Research Center, Taiwan, number BCRC11688) was directly implanted into the previous ferment for 3-10 days fermentation; wherein, the fermentation of these three kinds of bacteria was: yeast, *Lactobacillus*, and *Acetobacter*, and the order cannot be changed. Finally, in the case that the three bacteria in the ferment were not removed, if the ferment meets the specification of sugar content ranges with 2-10°, pH 2-4, alcohol <3%, etc., the fermentation is completed and obtain the final ferment. Then, the ferment was concentrated under reduced pressure at 45-70° C., and filtered through a 200-400 mesh sieve, and then 1-3% citric acid and 40-70% isomalto-oligosaccharide were added to adjust the specifications and then sterilized to obtain the *Actinidia chinensis* Planch ferment of the present invention. By microbial fermentation, the effect substance in fruits of *Actinidia chinensis* Planch is released in large quantities.

Example 2

Effect of the *Actinidia chinensis* Planch Ferment on Increasing the Superoxide Dismutase (SOD) Activity Superoxide dismutase (SOD) is an enzyme that catalyzes the dismutation (or partitioning) of the superoxide and converts them into oxygen and hydrogen peroxide. It is widely found in various animals, plants, and microorganisms. It is an important antioxidant in the body that protects cells exposed to oxygen. In the embodiment of the present invention, in order to compare whether the SOD activity contained in the *Actinidia chinensis* Planch ferment of the present invention is higher than that in the unfermented extract, the SOD activity was quantified by inhibiting the pyrogallol autooxidation reaction. First, the solution A and the solution B for the quantification were prepared, wherein the solution A was 1.2114 g of Tris(hydroxymethyl)aminomethane (Tris) and 37.2 mg of ethylenediaminetetraacetic acid (EDTA-2 Na) dissolved in 62.4 mL of 0.1 mole/L hydrochloric acid solution, and then be dissolved in pure water after dissolution to the total volume of 100 mL; and the solution B was 56.7 mg of pyrogallol dissolved in a small amount of 10 mmole/L hydrochloric acid solution, and then be dissolved in pure water after dissolution to the total volume of 100 mL. Next, 2.35 mL of the solution A was taken in a centrifuge tube, and 1.8 mL of pure water and 0.2 mL of each of the *Actinidia chinensis* Planch ferment of the present invention (experimental group) or the *Actinidia chinensis* Planch water extract (control group) were added, and the solutions were mixed well by vortex. Next, 0.15 mL of solution B was added into each tube, and the solutions were mixed gently and evenly, and then pour into the colorimetric tube to measure the absorbance of 325 nm at the initial time and the 1 minute after reaction; wherein, the group added 0.2 mL pure water was as the control Finally, calculate the SOD activity by the following formula:

$$SOD\ activity\ (U/mL) = \frac{\frac{\Delta A_{325} - \Delta A'_{325}}{\Delta A_{325}} \times 100\%}{50\%} \times 4.5 \times \frac{1}{V} \times D$$

$\Delta A_{325}$: Oxidation rate of pyrogallol
$\Delta A'_{325}$: Anti-oxidation rate of Tris by the sample
V: Volume of the sample
D: Dilution ratio of the sample The results of the effect of the *Actinidia chinensis* Planch ferment on increasing the superoxide dismutase activity were shown in FIG. 1. As showing in FIG. 1, after the three-staged fermentation, the SOD activity of the *Actinidia chinensis* Planch ferment is 3.6 times higher than that of the *Actinidia chinensis* Planch water extract, and the result indicates that the SOD activity of the *Actinidia chinensis* Planch ferment of the present invention can be effectively enhanced by the specific microbial fermentation step. The specific fermentation step can enhance the antioxidant activity of the fruits of *Actinidia chinensis* Planch, and can be used for preparing a composition for improving the antioxidant activity of the gastrointestinal tract, increasing the function of the gastrointestinal tract, and maintaining the normal operation of the gastrointestinal immune function.

Example 3

Effect of the *Actinidia chinensis* Planch Ferment on Increasing the Total Amount of Polyphenol Polyphenols are an antioxidant, and previous studies have indicated that polyphenols can inhibit the development of neurodegenerative diseases and some cardiovascular diseases. In the embodiment of the present invention, in order to compare whether the total amount of pilyphemol in the *Actinidia chinensis* Planch ferment of the present invention is higher than that in the unfermented extract, the Folin-Ciocalteu colorimetric assay was used to determine the total amount of polyphenol. The assay utilizes phosphomolybdic acid in the reagent to quantify the total amount of polyphenol, which phosphomolybdic acid would be reduced from $Mo^{6+}$ to $Mo^{5+}$ to form a blue compound, and the depth of the blue compound is positively correlated with the total amount of polyphenol. First, the *Actinidia chinensis* Planch ferment (experimental group) of the present invention and the *Actinidia chinensis* Planch water extract (control group) were respectively diluted with water and 100 mL of the diluted solutions were taken into a centrifuge tube, followed by adding 500 μL of Folin-Ciocalteu phenol reagent and mixing. After reacting for 3 minutes, 400 μL of 7.5% sodium carbonate was added into each centrifuge tube and mixed well to react for 30 minutes, and then 200 μL of each reaction solution was transferred into a 96-well plate, and the absorbance at 750 nm was measured. Among them, gallic acid was used as a standard to prepare a standard curve. 10 g of gallic acid was dissolved in water, and the standards were 0 μL/mL, 20 μL/mL, 40 μL/mL, 60 μL/mL, 80 μL/mL, and 100 μL/mL of gallic acid respectively. 100 μL of each standard solution was taken into a 10 mL centrifuge tube, and 500 μL of Folin-Ciocalteu phenol reagent was added and mixed well for 3 minutes reaction. Then, 400 μL of 7.5% sodium carbonate was added into each centrifuge tube and mixed well. After 30 minutes reaction, 200 μL of each reaction solution was taken in a 96-well plate, and the absorbance at 750 nm was measured to obtain a standard curve, and the total amount of polyphenol in the *Actinidia chinensis* Planch ferment of the present invention and the *Actinidia chinensis* Planch water extract were converted by a standard curve.

Figure 2:
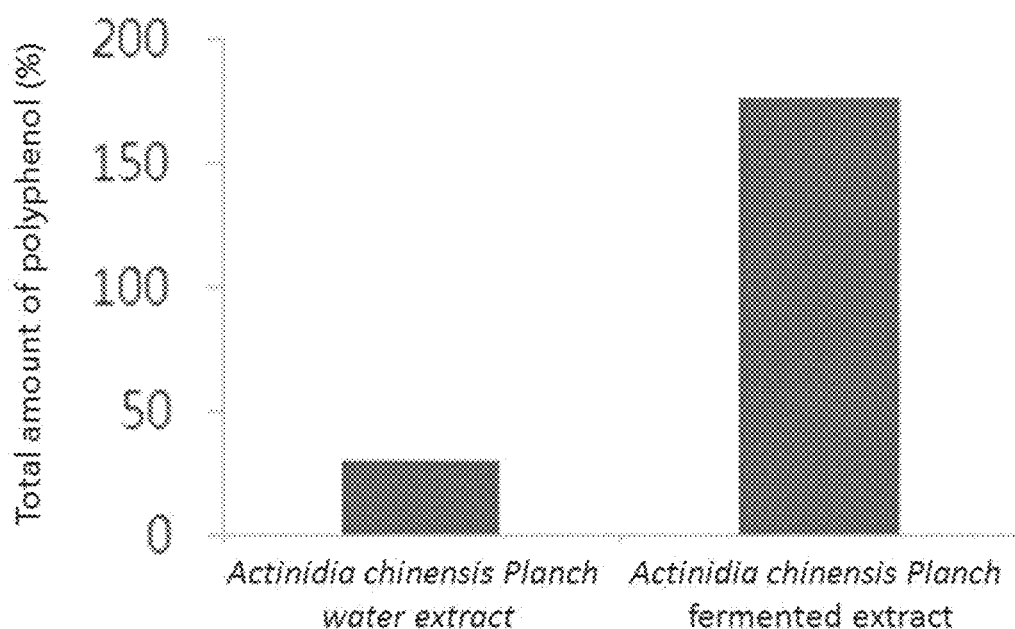
FIG. 2 shows a bar graph that the *Actinidia chinensis* Planch ferment increases the total amount of polyphenol.

The results of the effect of the *Actinidia chinensis* Planch ferment on increasing the total amount of polyphenol were shown in FIG. 2. As showing in FIG. 2, after the three-staged fermentation, the total amount of polyphenol of the *Actinidia chinensis* Planch ferment is 5.8 times higher than that of the *Actinidia chinensis* Planch water extract, and the result indicates that the total amount of polyphenol of the *Actinidia chinensis* Planch ferment of the present invention can be effectively enhanced by the specific microbial fermentation step. The specific fermentation step can enhance the antioxidant activity of the fruits of *Actinidia chinensis* Planch, and can be used for preparing a composition for improving the antioxidant activity of the gastrointestinal tract, increasing the function of the gastrointestinal tract, and maintaining the normal operation of the gastrointestinal immune function.

Example 4

Effect of the *Actinidia chinensis* Planch Ferment on Increasing the Anti-Glycation Activity In the embodiment of the present invention, in order to compare whether the anti-glycation activity of the *Actinidia chinensis* Planch ferment of the present invention is higher than that of the unfermented extract, the efficacy of samples on inhibiting D-fructose producing glycated reaction on bovine serum albumin (BSA) was carried out to quantify the anti-glycation activity. First, 0.25 mL of the 20% (v/v) diluted *Actinidia chinensis* Planch water extract (control group) or the 20% (v/v) diluted *Actinidia chinensis* Planch ferment of the present invention (experimental group) was added into a centrifuge tube, and 0.25 mL of 60 mg/mL BSA solution containing 60 mg of 0.06% $NaN_3$ (configured in 200 mM sodium phosphate buffer, pH 7.4) was added into each centrifuge tube and mixed well, and then 0.1 mL of each mixed solution was measured for the fluorescence at 360 nm excitation light and 460 nm emission light and the values were used as the starting point of the reaction. Next, 0.45 mL of each mixed solution was incubated at 50° C. for 24 hours, and then 0.1 mL of each of them was taken out for the measurement of fluorescence, and the values were as the ending point of the reaction. An equivalent amount of 3 mM aminoguanidine (AG, configured in 200 mM sodium phosphate buffer) was used to re-dissolve in the solvent to an equal volume as a positive control; wherein aminoguanidine is known to have the effect of inhibiting glycation. Finally, the efficiency of the ability to scavenge advanced glycation end products (AGEs) is calculated by the following formula to represent the anti-glycation activity.

$$Anti\text{-}glycation\ activity = \left[ 1 - \frac{Fluorescence\ sample_{24hr} - Fluorescence\ sample_{Chr}}{Fluorescence\ control_{24hr} - Fluorescence\ control_{Chr}} \right] \times 100\%$$

Figure 3:
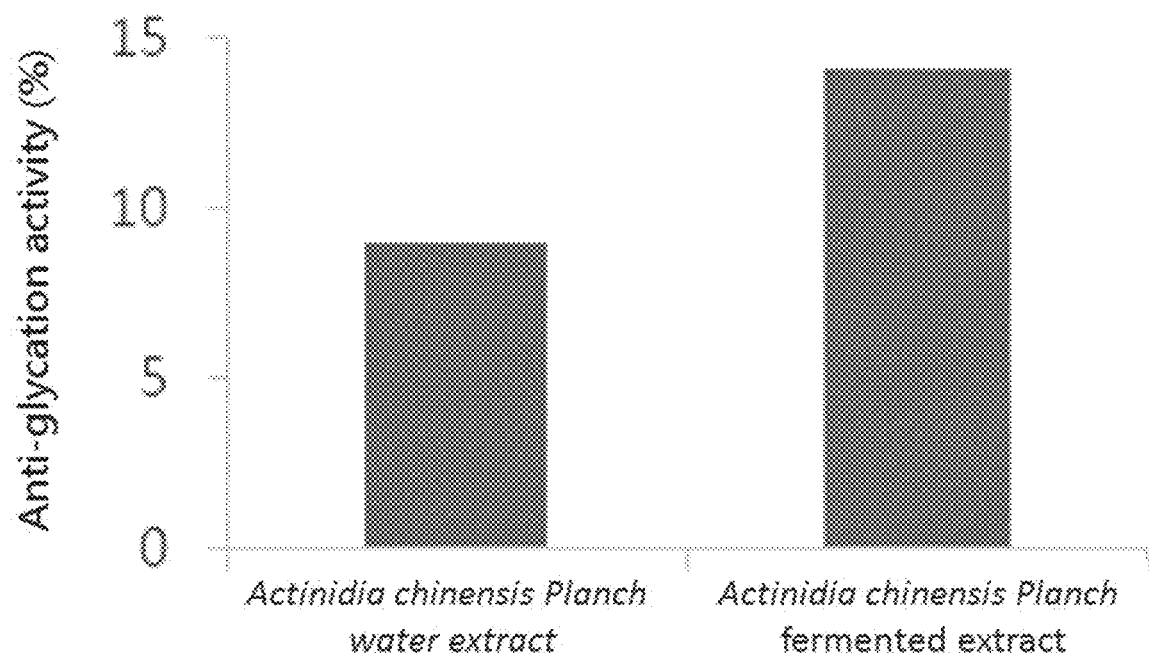
FIG. 3 shows a bar graph that the *Actinidia chinensis* Planch ferment increases the anti-glycation activity.

The results of the effect of the *Actinidia chinensis* Planch ferment on increasing the anti-glycation activity were shown in FIG. 3. As showing in FIG. 3, after the three-staged fermentation, the ability to scavenge advanced glycation end products of polyphenol of the *Actinidia chinensis* Planch ferment is 1.4 times higher than that of the *Actinidia chinensis* Planch water extract, and the result indicates that the ability to scavenge advanced glycation end products of the *Actinidia chinensis* Planch ferment of the present invention can be effectively enhanced by the specific microbial fermentation step. The specific fermentation step can enhance the anti-glycation activity of the fruits of *Actinidia chinensis* Planch, and then contributes to delay the progression of chronic diseases and aging.

Example 5

Effect of the *Actinidia chinensis* Planch Ferment on Increasing the Activity of Proteolytic Enzymes In the embodiment of the present invention, in order to compare whether the activity of a proteolytic enzyme of the *Actinidia chinensis* Planch ferment of the present invention is higher than that of the unfermented extract, the Skim Milk Agar (purchased from HIMEDIA, India) was used to quantify the activity of the proteolytic enzyme. The kind of agar could be used to test whether something has the ability to break down proteins. If the protein is decomposed, a transparent circle would be generated around the samples. First, a Skim Milk Agar solution (the purchased powder contains 2.8% (w/v) skim milk powder, 0.5% (w/v) casein hydrolysate, 0.25% (w/v) yeast extract, 0.1% (w/v) glucose, and 1.5% (w/v) agarose gel) was prepared and autoclaved, and then the temperature of it was lowered to 40-50° C., and it was poured into a dish to make a plate. Next, the *Actinidia chinensis* Planch water extract and the *Actinidia chinensis* Planch ferment of the present invention were separately diluted 10 times, and the two sample dilutions with the same concentration were dropped onto two different Skim Milk Agars, and cultured in an incubator at 37° C. for 24 hours, and then the size of the transparent circles produced by each sample were observed and recorded; wherein, water was used as a blank control group.

Figure 4:
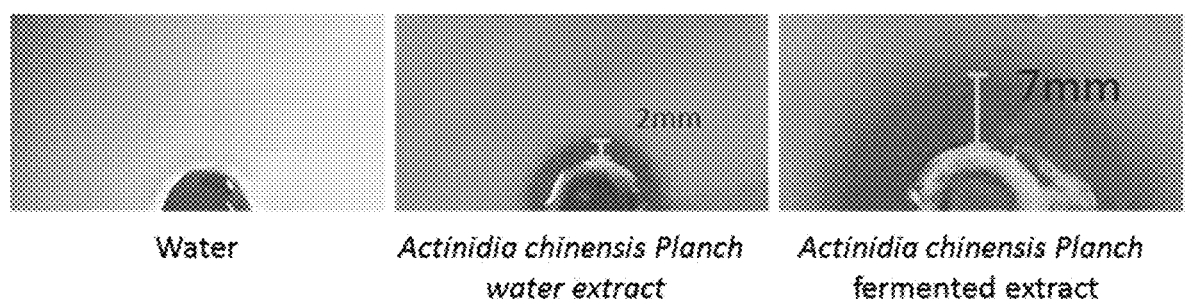
FIG. 4 shows a graph that the *Actinidia chinensis* Planch ferment increases the activity of proteolytic enzymes.

The results of the effect of the *Actinidia chinensis* Planch ferment on increasing the activity of proteolytic enzymes were shown in FIG. 4. As showing in FIG. 4, after the three-staged fermentation, the size of the transparent circles produced by the *Actinidia chinensis* Planch ferment on the Skim Milk Agar is 3.5 times higher than that of the *Actinidia chinensis* Planch water extract, and the result indicates that the activity of a proteolytic enzyme of the *Actinidia chinensis* Planch ferment of the present invention can be effectively enhanced by the specific microbial fermentation step, and to increase the function of gastrointestinal digestion to avoid discomfort caused by indigestion.

Example 6

Effect of the *Actinidia chinensis* Planch Ferment on Improving the Gastrointestinal Digestion In order to confirm the effect of the *Actinidia chinensis* Planch ferment of the present invention on improving the gastrointestinal digestion, 7 adults with functional dyspepsia (FD) were recruited to take 5-20 mL of the *Actinidia chinensis* Planch ferment of the present invention after daily lunch. The questionnaire for the Nepean Dyspepsia Index (NDI, see World J Gastroenterol. 2009 Jul. 7; 15(25): 3173-7) was completed by the subjects to feedback and analyze before taking the *Actinidia chinensis* Planch ferment of the present invention, taking it for 2 weeks, and taking it for 8 weeks; wherein, the Nepean Dyspepsia Index was created by Talley et al., and the index contains 25 items and is divided into five areas: stress and sleep, daily life intervention, diet, knowledge and self-control, and work or study. The scale is a tool for determining the health-related quality of life (HRQL) of the digestive system, which provides a measure of the symptoms of dyspepsia and an HRQL that is specific for the assessment of dyspepsia.

Figure 5:
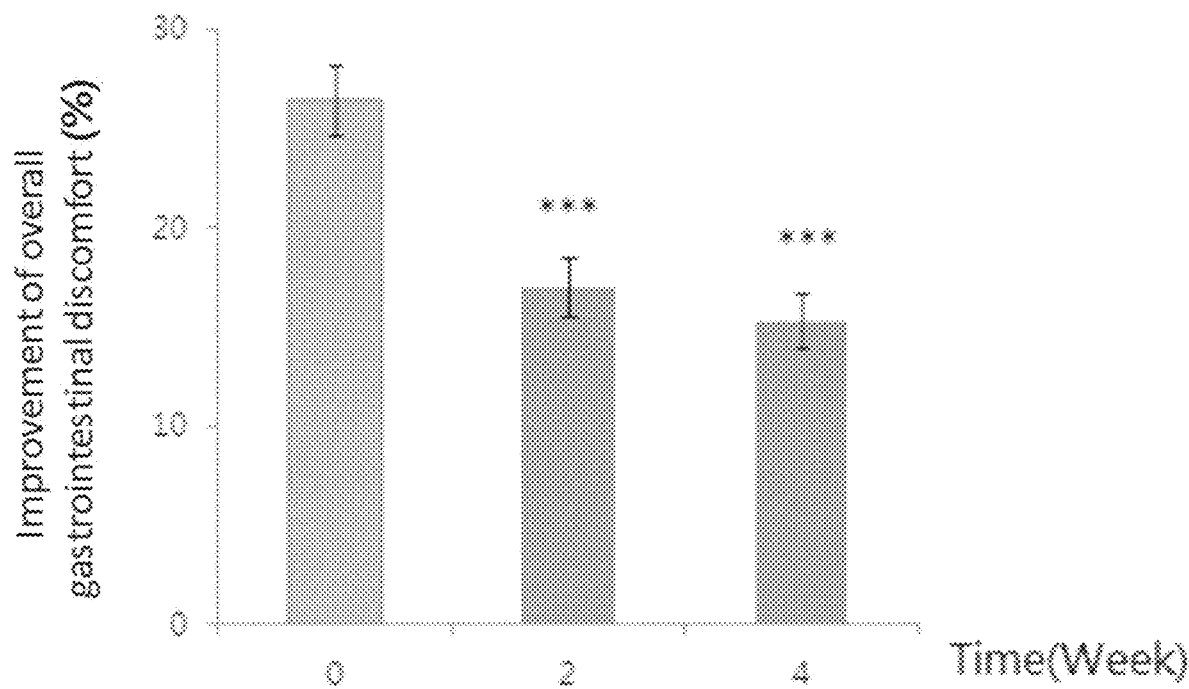
FIG. 5 shows a bar graph that the *Actinidia chinensis* Planch ferment improves the gastrointestinal discomfort symptoms of the bodies. *** $p<0.001$.
Figure 6:
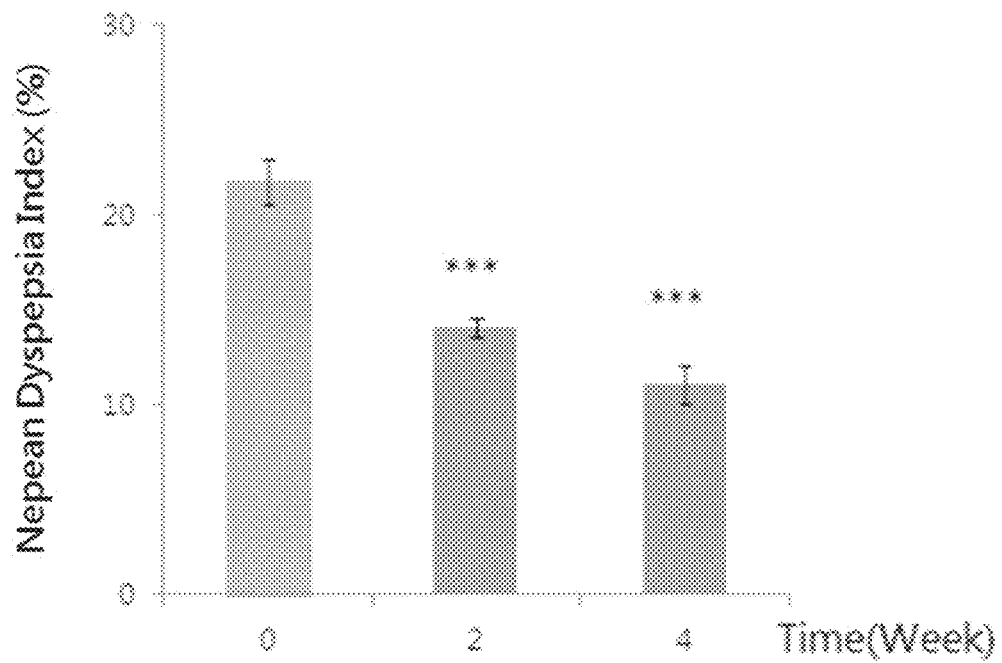
FIG. 6 shows a bar graph that the *Actinidia chinensis* Planch ferment improves the Nepean Dyspepsia Index of the bodies. *** $p<0.001$.

The results of the effect of the *Actinidia chinensis* Planch ferment on improving the gastrointestinal discomfort symptoms of the bodies were shown in FIG. 5; the results of the effect of the *Actinidia chinensis* Planch ferment on improving the Nepean Dyspepsia Index of the bodies were shown in FIG. 6. As showing in FIGS. 5 and 6, after taking the *Actinidia chinensis* Planch ferment of the present invention for 4 weeks, the overall gastrointestinal symptoms of up to 42% could be improved; and according to the Nepean Dyspepsia Index, the *Actinidia chinensis* Planch ferment of the present invention can improve the symptoms of gastrointestinal discomfort up to 49%; and the improvement ratio of the subjects was as high as 100% (data not shown). The results indicate that the *Actinidia chinensis* Planch ferment of the present invention has an excellent effect on improving the overall gastrointestinal dyspepsia condition. In addition, after taking the *Actinidia chinensis* Planch ferment of the present invention for 4 weeks, the diversity of intestinal flora can be increased by 1.5 times, and the improvement ratio of the subjects was as high as 60% (data not shown). It is known that an increase in the diversity of intestinal flora can reduce the risk of many diseases, including gastrointestinal related diseases. Therefore, from these results, it is revealed that the *Actinidia chinensis* Planch ferment of the present invention has an excellent ability to improve gastrointestinal discomfort and increase the diversity of gastrointestinal flora to effectively be used for the gastrointestinal care and the digestion.

In summary, the fruits of *Actinidia chinensis* Planch fermented by the three-staged fermentation of the present invention by yeast, *Lactobacillus*, and *Acetobacter* can effectively increase the SOD activity, increase the total amount of polyphenol, enhance the ability of scavenging advanced glycation end products, increasing the activity of proteolytic enzymes, improving gastrointestinal dyspepsia, and increase the diversity of gastrointestinal flora. The *Actinidia chinensis* Planch ferment of the present invention has better effect than the *Actinidia chinensis* Planch water extract, and can be more effectively used for preparation a pharmaceutical compositions for increasing antioxidant activity, increasing anti-glycation activity, increasing the activity of proteolytic enzymes, improving gastrointestinal dyspepsia, and increasing gastrointestinal flora, and to effectively improve the function of the gastrointestinal tract to maintain the normal operation of the gastrointestinal immune function and to slow down the progression of chronic diseases and aging, as well as to increase the function of gastrointestinal digestion, and to be used for the gastrointestinal care and maintain normal function of the intestines.

What is claimed is:

1. A method of increasing an antioxidant activity and an anti-glycation activity in a subject in need thereof, comprising administering to the subject in need thereof an effective amount of an *Actinidia chinensis* Planch ferment, wherein the *Actinidia chinensis* Planch ferment is obtained by steps of:

extracting *Actinidia chinensis* Planch with water to obtain an *Actinidia chinensis* Planch extract;

fermenting the *Actinidia chinensis* Planch extract sequentially with 0.01-0.5% (v/v) of *Saccharomyces cerevisiae* for 1-2.5 days, 0.01-0.25% (v/v) of *Lactobacillus plantarum* for 1-3 days, and 3-10% (v/v) of *Acetobacter aceti* for 3-10 days; and separating the *Actinidia chinensis* Planch ferment;

wherein increasing the antioxidant activity and the antiglycation activity are determined by comparing to that of the unfermented *Actinidia chinensis* Planch extract.

2. The method according to claim 1, wherein increasing the antioxidant activity results from increasing the activity of superoxide dismutase or from increasing the total polyphenol content in the *Actinidia chinensis* Planch ferment, wherein the increase of the activity of superoxide dismutase or the increase of the total polyphenol content in the *Actinidia chinensis* Planch ferment is determined by comparing to that of the unfermented *Actinidia chinensis* Planch extract.

* * * * *